United States Patent [19]

Frank et al.

[11] Patent Number: 5,265,615
[45] Date of Patent: Nov. 30, 1993

[54] METHOD AND APPARATUS FOR CONTINUOUS MEASUREMENT OF CARDIAC OUTPUT AND SVR

[76] Inventors: Eyal Frank, Azmaut 37, Bat-yam; Yuval Raich, Faran, D.N. Arava, both of Israel

[21] Appl. No.: 992,756

[22] Filed: Dec. 18, 1992

[51] Int. Cl.⁵ ............................................. A61B 5/021
[52] U.S. Cl. ...................................... 128/672; 128/713
[58] Field of Search .............................. 128/672–686, 128/713, 734, 691–694, 670–671

[56] References Cited

U.S. PATENT DOCUMENTS

| | | | |
|---|---|---|---|
| 4,437,469 | 3/1984 | Djordjevich et al. | 128/734 X |
| 4,562,843 | 1/1986 | Djordjevich et al. | 128/734 X |
| 4,807,638 | 2/1989 | Sramek | 128/734 X |
| 5,183,051 | 2/1993 | Kraidin et al. | 128/713 X |

FOREIGN PATENT DOCUMENTS

| | | | |
|---|---|---|---|
| 000367 | 1/1990 | PCT Int'l Appl. | 128/713 |
| 006633 | 4/1992 | PCT Int'l Appl. | 128/713 |
| 1289450 | 2/1987 | U.S.S.R. | 128/713 |

*Primary Examiner*—Kyle L. Howell
*Assistant Examiner*—Angela D. Sykes
*Attorney, Agent, or Firm*—Oblon, Spivak, McClelland, Maier & Neustadt

[57] ABSTRACT

A method of continuously monitoring cardiac output and SVR of a patient by analyzing the blood pressure signal. The signal can be measured directly by the use of catheters placed into various arteries, in particular a radial artery or a femoral artery, or non-invasive methods such as electrooptic means, or using a piezoelectric pressure transducer. Various parameters are extracted from the blood pressure signal waveform in order to calculate the cardiac output of the patient and other hemodynamic data.

18 Claims, 10 Drawing Sheets

METHOD AND APPARATUS FOR CONTINUOUS MEASUREMENT OF CARDIAC OUTPUT AND SVR

BACKGROUND OF THE INVENTION

1. Field of the Invention

The present invention relates to a new method and apparatus for monitoring and/or measuring cardiac output and SVR of a patient by analyzing a blood pressure signal which contains various parameters related to particular characteristics of the patient's vascular system.

2. Description of the Related Art

Cardiac output is the ultimate expression of cardiovascular performance. The term "cardiac output" indicates the quantity of the blood ejected each minute by either the right or left ventricle. Absolute cardiac output in an in vivo pulsating flow system is the product of the stroke volume and the heart rate frequency per minute. Stroke volume quantitatively defines the beat-to-beat volumetric performance of the heart as an intermittent flow generator or pulsating pump. The performance of the pump on a beat-to-beat basis and thus the magnitude of stroke volume is determined by three major independent variables: pre-load, contractility and after-load. Each major determinant of stroke volume has its own subsets of major and minor independent variables. The integrated modulation of all variables contributes to the stroke volume generated by the ventricles for each heartbeat. The parameters associated with cardiac output are useful in that they can be employed to evaluate the overall cardiac status of critically ill patients, patients with suspected cardiovascular and pulmonary diseases, patients undergoing surgery, and any situations that require blood pressure monitoring.

The radial stretch of the ascending aorta involved in the ejection of blood by the left ventricle initiates a pressure wave which propagates down the aorta and its various branches. The pressure wave travels with a finite velocity that is considerably faster than the actual forward movement of the blood itself, and is a wave which pulsates as it reaches the peripheral arteries. The velocity of transmission of the pressure wave varies inversely with the vascular capacitance of the arteries. Also, it is known that the velocity increases progressively as the pulse wave travels from the ascending aorta toward the peripheral regions. The arterial pressure signal contour becomes distorted as the wave is transmitted down the arterial system. There are three major changes which occur in the arterial pulse contour as the pressure wave moves forward. The first is that the high frequency components of the pulse, such as those corresponding to the dicrotic notch, are filtered and soon disappear. The second change is that the systolic portions of the pressure wave become narrowed and elevated. Third, a "hump" may become prominent on the diastolic portion of the pressure wave.

In elderly patients with less compliant arteries, the pulse wave may be transmitted virtually unchanged from the aorta to the periphery. The reason for this change is controversial. A common explanation is based on the concept that the pulse wave is reflected from branch points back toward the aortic arch to thereby set up pressure oscillations. In an elastic tube, a traveling pressure wave is reflected to some extent wherever there is discontinuity in the system. If the tube is completely blocked, reflection of the pulse wave energy is complete (and will be 180° out-of-phase). If a pressure wave travels with increasing velocity toward the periphery and reflects back from regions where many branches occur over a short distance, the oncoming pressure wave is distorted, attaining a higher peak pressure and wider fluctuations following the peak, while at the root of the aorta, the initial upstroke of pressure is extremely rapid.

During the remainder of the systolic period (or "systole"), the pressure wave is rounded or "dome" shaped. The end of systole is clearly marked by a sharp dicrotic notch accompanying closure of semilunar valves. During the diastolic run-off, the pressure declines almost linearly. The pressure descends rapidly, and during the run-off period there is an additional wave called the dicrotic wave.

In addition to distortion of the waveform resulting from reflected waves, changes in the pulse waveform can be visualized in terms of its frequency contents. The transmission velocity of the high frequencies of the signal is faster than that of the low frequencies. Under these circumstances, the more rapidly traveling high frequency waves may produce increased peaking of the pressure pulse and corresponding deformation of the remainder of the pulse.

Various methods are known in the art for measuring cardiac output, a common approach involving a thermodilution technique in which a solution colder than body temperature is injected into the right atrium through a catheter and the resulting drop in blood temperature at the catheter tip indicates an amount of blood flowing around the tip. This method is invasive, however, and thus involves risks to the patient as it has the possibility of damaging the anatomical structures through which the catheter is threaded. Complications associated with pulmonary artery catheterization include pulmonary artery rupture, balloon rupture, sepsis, air embolism, etc.

Other conventional ways of determining cardiac output include thoracic bioimpedance and continuous wave Doppler ultrasonography. These two techniques are non-invasive, and are thus preferred for patients with high-risk vulnerability to the invasive procedures such as thermodilution estimation methods. In the bioimpedance method, changes in resistance to microcurrents injected into a patient are measured in order to calculate stroke volume, i.e., the amount of blood pumped in a single beat of the heart. The method therefore involves a pulse-by-pulse determination of cardiac output whereby four pairs of surface ECG electrodes are placed on the neck and chest of a patient. The outer pairs of electrodes inject a 70 KHz, 2.5 mA current into the thoracic tissue and the current is then sensed with the inner pairs of electrodes. The resistance to the injected current is dependent upon the fluid characteristics of the thoracic volume. Pulsating changes in thoracic resistance (bioimpedance) are then timed to the ventricle electrical depolarization and mechanical systole.

Continuous wave suprasternal Doppler ultrasound uses a Doppler transducer placed in the suprasternal notch directed toward the ascending aorta. The Doppler probe measures the aortic blood velocity. The integral of aortic systolic blood velocity multiplied by the cross sectional area of the aorta gives the stroke volume.

Other methods of cardiac output measurement are based upon the Fick principle. This method is simply an application of the law of conservation of mass, whereby according to this principle, the rate of uptake or release of substance to or from blood at the lung is equal to the blood flow past the lung and the content difference of the substance at each side of the lung. This method is most commonly used with oxygen as the analyzed substance. By means of in-dwelling catheters, arterial and venous blood samples were obtained and these samples were analyzed on a blood gas analyzer to obtain the oxygen saturation and the partial pressure of oxygen.

The Fick technique has the disadvantage that the measurements are complex and can often require an entire day of analysis before cardiac output can be ascertained. This makes the Fick technique undesirable in real-time applications where quick results are required in order to keep the patient in a stable condition.

There has been disclosed in the prior art, a technique for monitoring system vascular resistance (SVR) using derivative calculations of a blood pressure signal of a patient. In this method, the signal is differentiated and the points of greatest slope in the systolic portions are determined and then divided into the pressure which exists at these points. Such a calculation is proportional to the system vascular resistance, and multiplication by a resistance factor will yield the SVR value. However, the present inventors have discovered that this method may lead to inaccurate results in that the analysis of the blood pressure waveform does not take into account various factors which may lead to undesirable results. The inventors have found that the arterial waveform inherently contains various "artifacts" which cause errors in measurement of cardiac output. These "artifacts" are due to variable characteristics of the cardiovascular system such as different arterial capacitances of patients' arteries, reflected waves which cause aberrations in the signal, and also various damping characteristics of the waveform. There has thus been a need in the prior art for a technique which overcomes these drawbacks.

SUMMARY OF THE INVENTION

It is therefore an object of the present invention to provide a new method and apparatus for examining and indicating the status of the cardiovascular system of a subject, cardiac output, SVR and all the hemodynamic data which can be calculated from the parameters associated with the arterial waveform such as stroke volume and the index data of cardiac output.

Another object of the present invention is to provide a method and apparatus which can be used with non-invasive techniques for monitoring a blood pressure signal.

A further object of the invention is to provide more accurate measurements of the cardiovascular parameters with a fast analysis time and an apparatus which is inexpensive to use.

A still further object of the invention is to alleviate the need for having a trained operator to monitor cardiac output, and also to provide wide patient acceptability.

The present invention accomplishes the above objects by providing a novel method and apparatus for analyzing a blood pressure signal in order to estimate the overall cardiac performance of a patient. A blood pressure monitoring transducer, which can be any of a number of known transducers which are commonly used in the art, continuously monitors the blood pressure signal of a patient which is then converted to a digital form. After low-pass filtering, a waveform analyzer extracts a number of different parameters associated with the particular blood pressure signal, and calculations are then performed based on these extracted parameters. The significance of the invention is that only the necessary parameters are extracted while the undesirable "artifacts" are ignored. The invention is therefore able to achieve more accurate estimations of cardiac output and SVR by analyzing the contours of the patient's blood pressure waveform.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
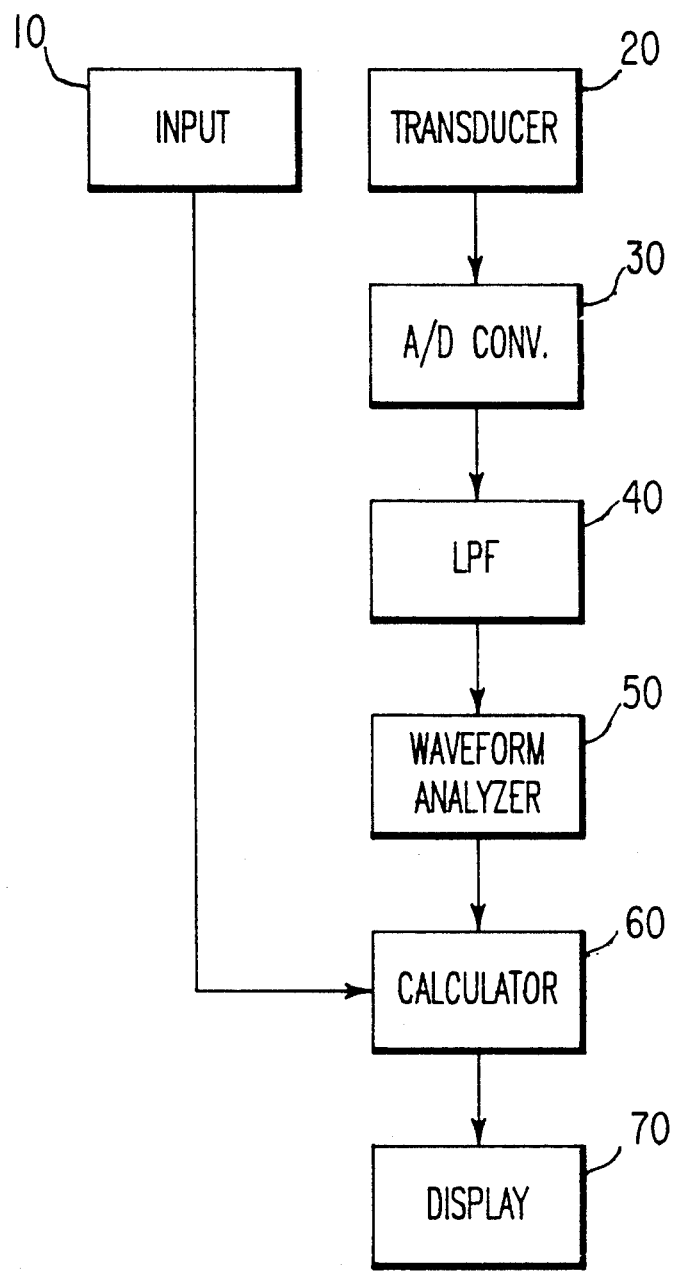
FIG. 1 represents an overall structural arrangement and interconnection of the various elements used for analyzing a blood pressure signal.

Referring now to the drawings, and more particularly to FIG. 1 thereof, there is shown a block diagram representative of the overall arrangement of the present invention. As shown in FIG. 1, a hardware connection of the various elements used in the calculation of cardiac output and SVR includes a transducer 20 which is part of a well-known blood pressure monitoring device. The transducer is connected to an A/D converter 30 which is in turn connected to low-pass filter (LPF) 40. The output of LPF 40 is connected to the input of waveform analyzer 50. Analyzer 50 is then connected to calculator 60 which can be, for example, a minicomputer. Calculator 60 also has a second input connected to input device 10, which can be a keyboard or any equivalent input device well known to those ordinarily skilled in the art. The output of calculator 60 is connected to display 70 for outputting the values calculated by calculator 60 in visual form.

The overall scheme of the system of the inventive method and apparatus will next be described. The blood pressure monitoring device which includes transducer 20 is used for generating a signal waveform representative of the patient's pulsating blood pressure which is then input to analog-to-digital converter 30 and then low-pass filtered in LPF element 40. The filter is used to smooth the electrical signal and remove noise components in the signal. The monitoring device can be either of the invasive or non-invasive type, and is not critical to the invention. However, as discussed above in regard to the invasive techniques for estimating cardiac output, the non-invasive techniques are often preferable as they involve less risk to the patient. It is to be understood, however, that the inventive method and apparatus can be practiced with either technique.

Next, waveform analyzer 50 extracts various parameters of the arterial waveform which are used for performing calculations in calculator 60, as will be described in more detail below. The input device 10 enables the manual input of the body surface area (BSA) of a patient by the operator, while display device 70 is used for the output of the calculated parameters which are calculated in calculator 60. Body surface area is calculated in a known manner based on the patient's height and weight.

Figure 2:
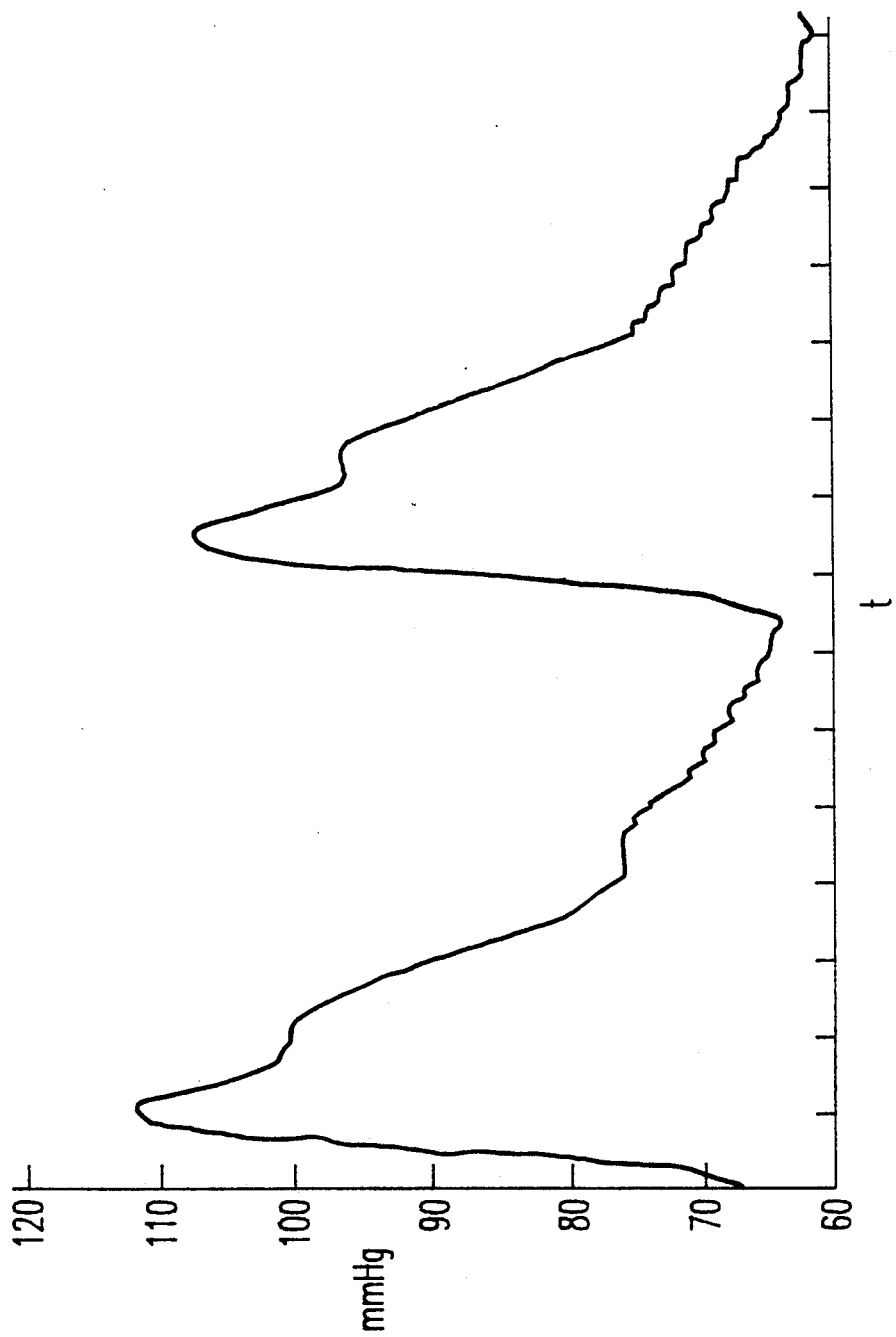
FIG. 2 represents an unfiltered arterial waveform representative of the blood pressure signal.
Figure 3:
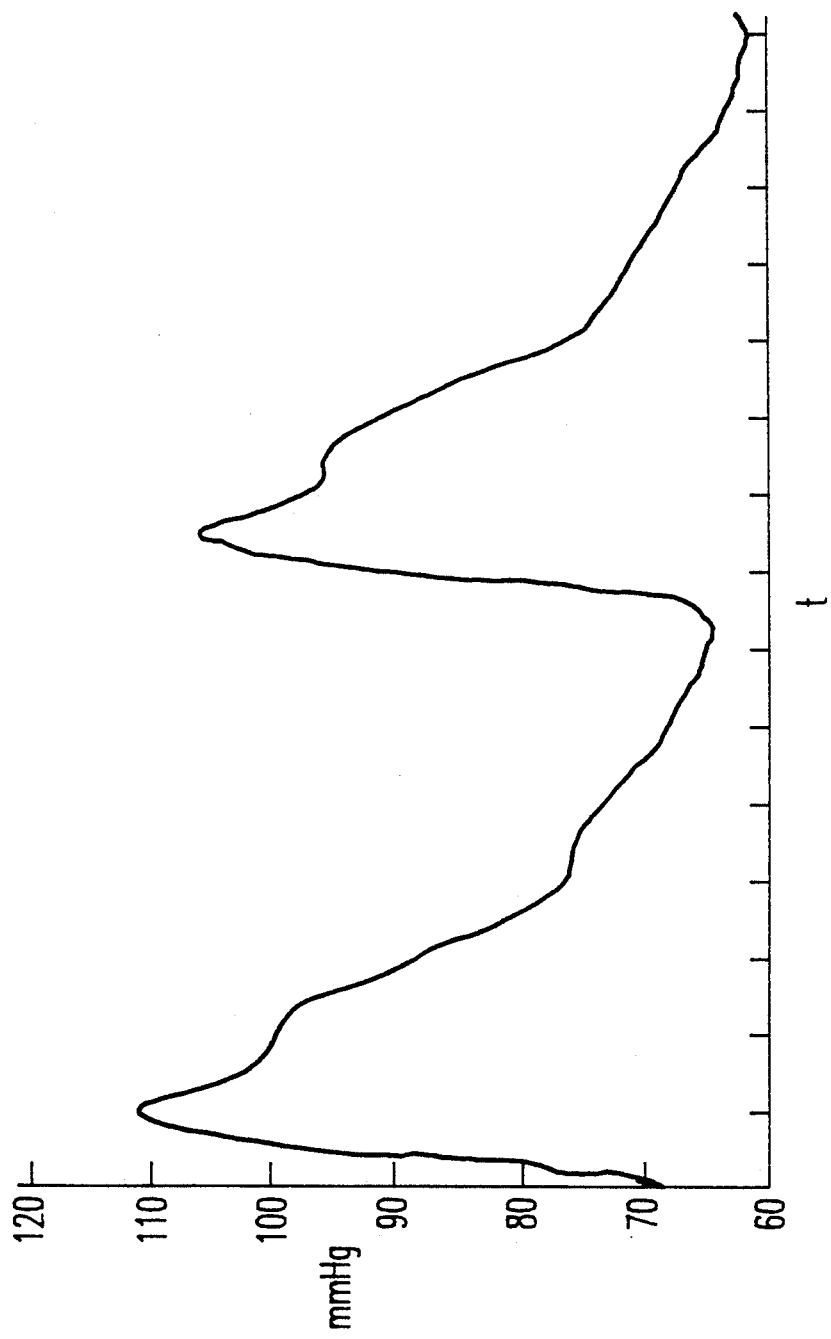
FIG. 3 shows the arterial waveform of FIG. 2 after low-pass filtering.

Referring now to FIG. 2, there is shown an arterial waveform of the blood pressure signal as represented on a coordinate axis graph whereby the pressure in millimeters of mercury is located on the y-axis and time along the x-axis. This waveform can be displayed on an oscilloscope if so desired, but is not necessary to the invention. As can be seen from FIG. 2, the waveform signal is a continuous chain of successive peaks (although only two are shown for purposes of simplification), and these peaks and valleys correspond to the systolic (i.e., dilation) and diastolic (i.e., contraction) portions of the patient's heartbeat. As can be seen from FIG. 2, there are distortions which exist at the tail end of the diastolic pressure just before a pressure peak corresponding to the systolic portion of the waveform. Upon low-pass filtering, as shown in FIG. 3, such aberrations in the arterial waveform are removed. FIG. 2 shows two different peaks of a patient. Each peak has different values of systolic, diastolic and average blood pressure, as well as different stroke volume (SV) and SVR. Each signal is an independent unit on which all calculations can be performed. The outputs can be time-averaged by a user.

Figure 4:
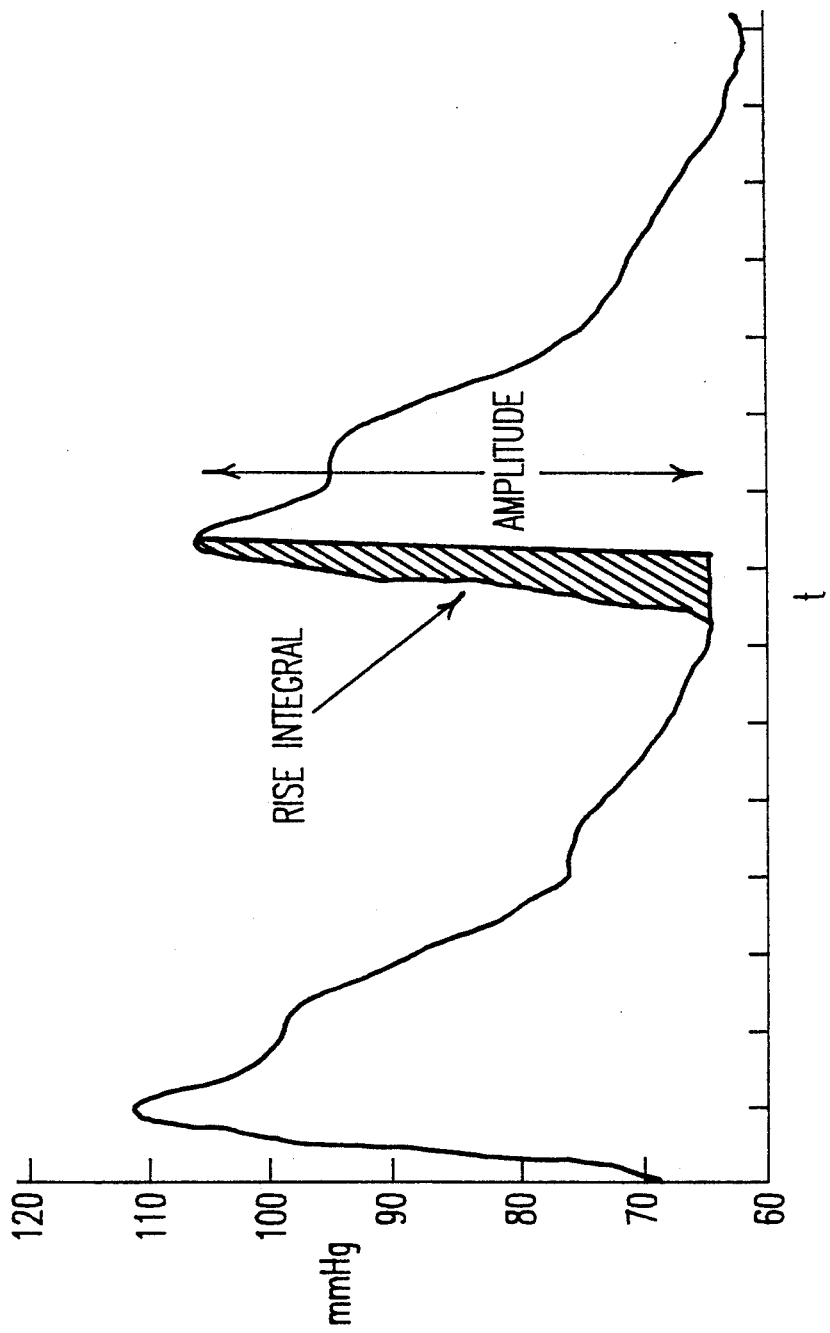
FIG. 4 illustrates the low-pass filtered waveform, and more particularly indicates the rise time integral and the amplitude of one of the systolic portions of the signal.

FIG. 4 illustrates graphically the amplitude and rise integral parameters of the arterial waveform for use in the calculations performed in calculator 60. As shown, the rise integral is determined based on the area under the curve from the lowest point in the diastolic period to the peak pressure occurring at systole. The vertical distance corresponding to these two points is detected as the amplitude of the waveform.

Figure 5:
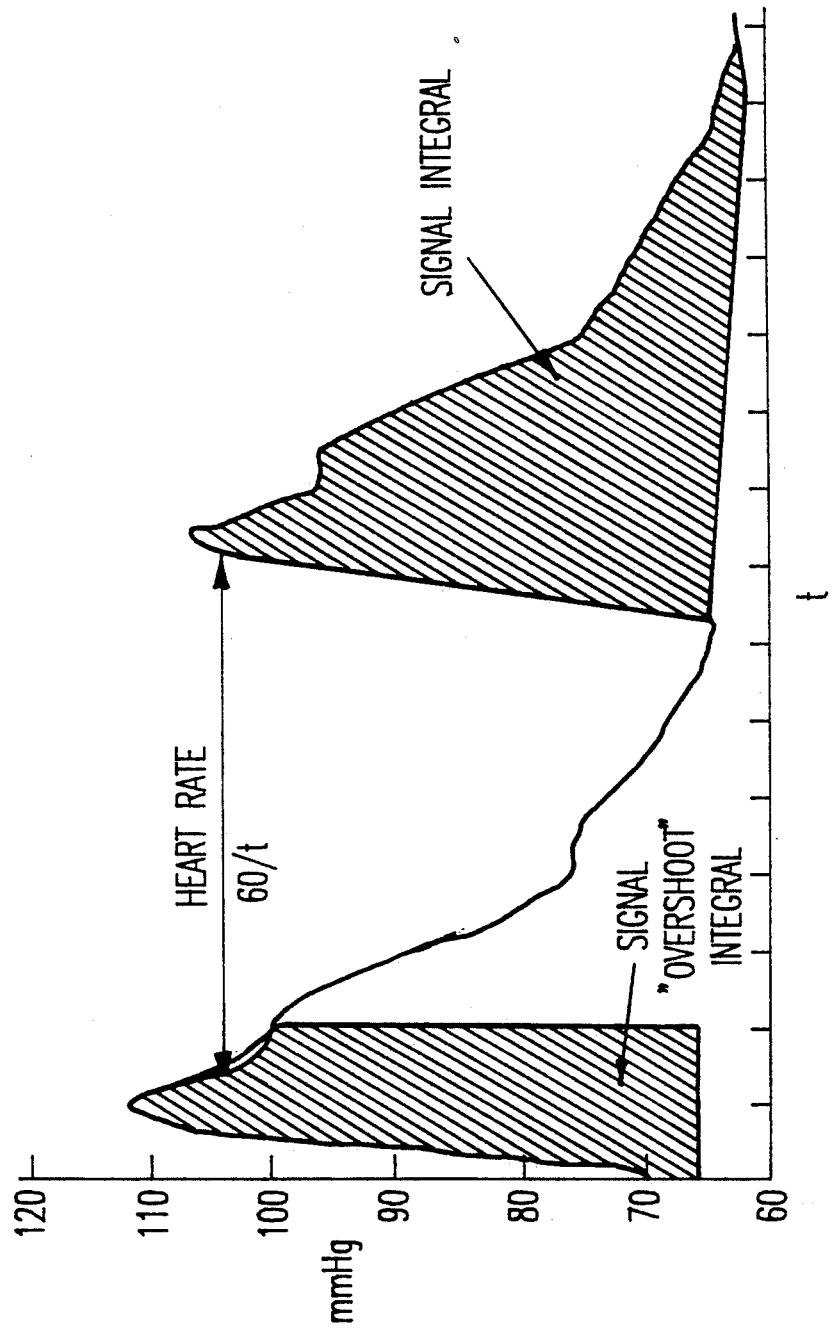
FIG. 5 illustrates the arterial waveform shown in FIG. 2 and additional parameters of the waveform which are calculated.

In FIG. 5, the signal "overshoot" integral is determined based upon the area under the waveform curve corresponding to the low point in the diastolic period up until the time at which the dicrotic notch is detected. "Overshoot" is a situation of pressure reflection from the blood arteries, which is dependent upon a specific artery and completely unrelated to systemic pressure. It should also be noted that arterial capacitance is a parameter related to arterial flexibility. The heart rate is shown as being equal to a set time period (i.e., 60 seconds) divided by the time interval existing between two successive peaks of the waveform signal. The signal integral is shown as being the area under the waveform curve from the beginning of the systolic period to the end of the diastolic period.

Figure 6:
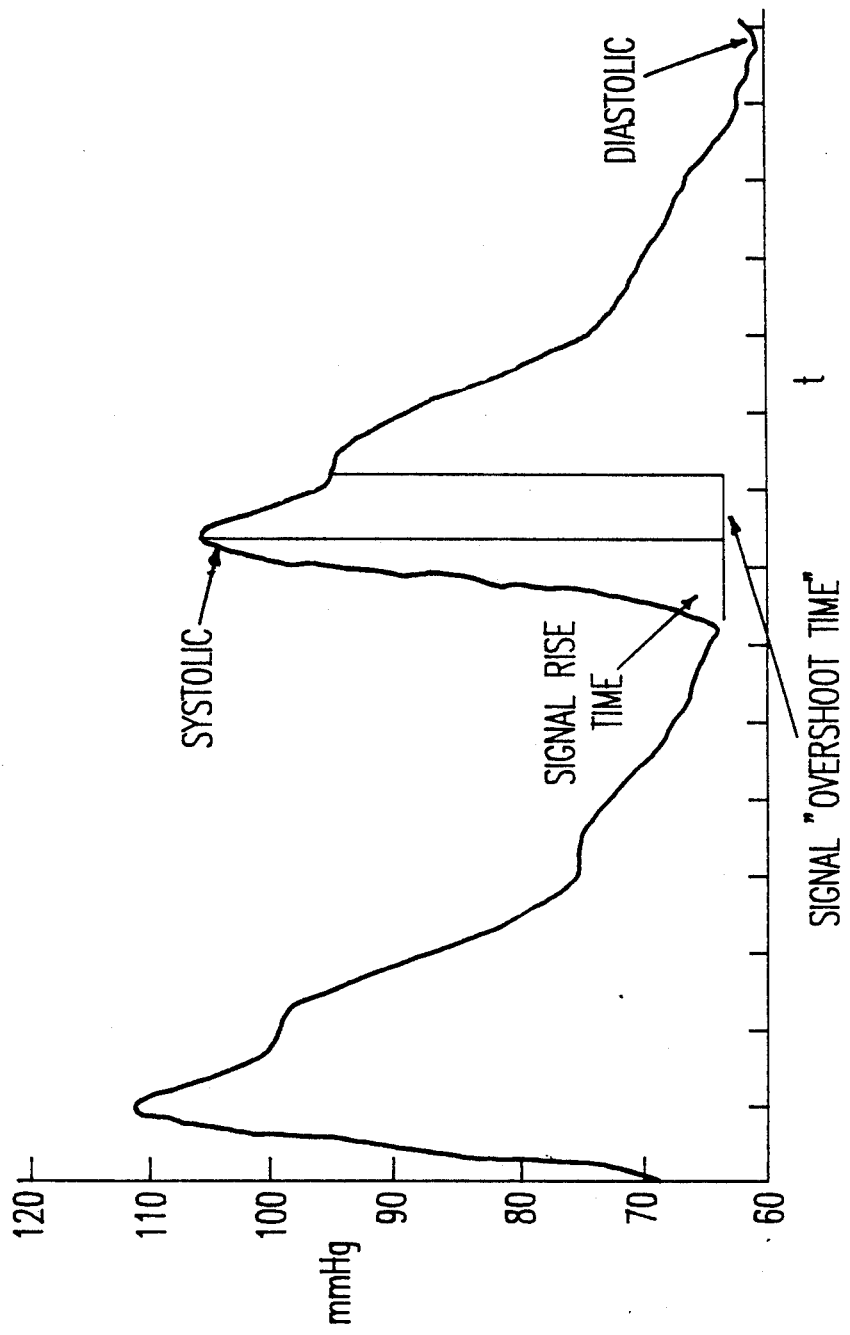
FIG. 6 illustrates still further characteristics of the waveform which are analyzed according to the invention.
Figure 7:
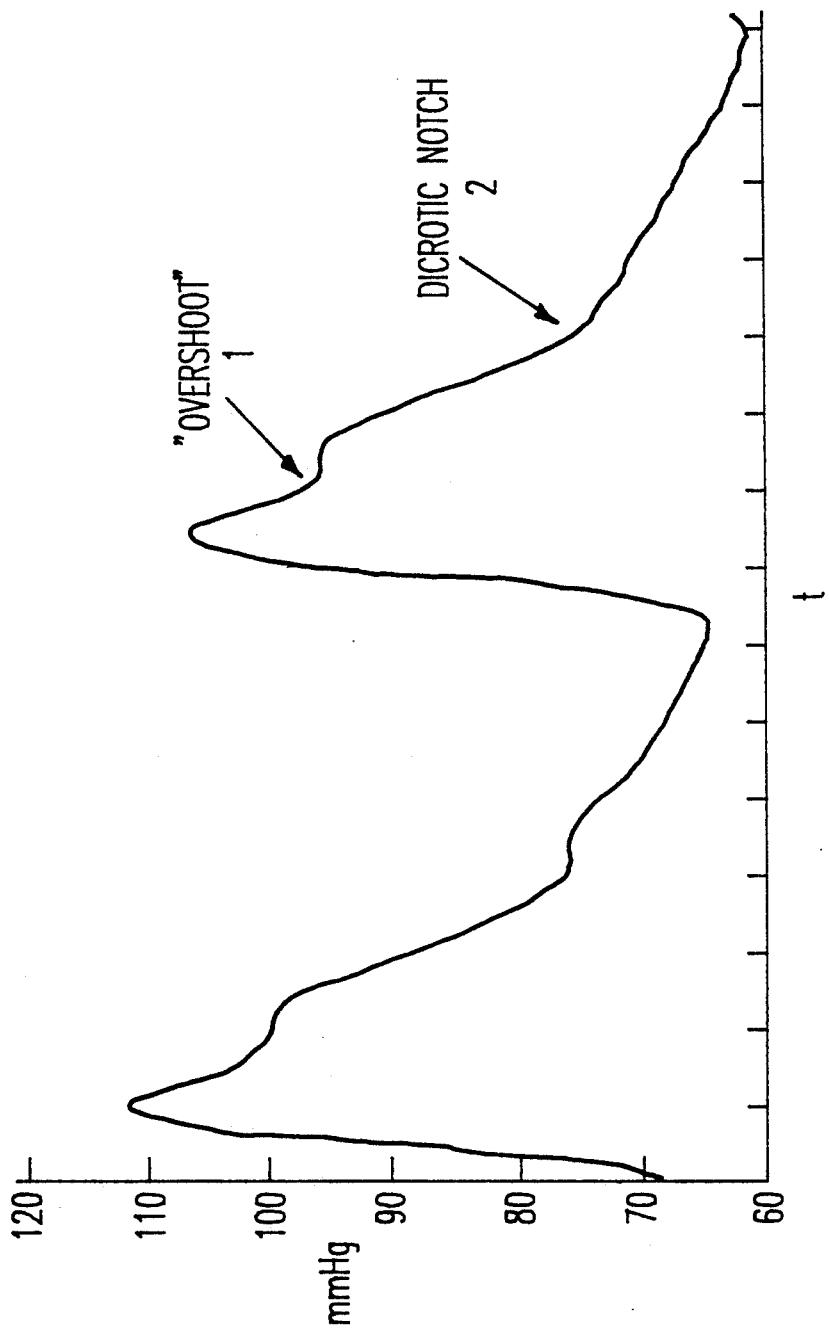
FIG. 7 illustrates the concept of "overshoot" and also dicrotic notch.
Figure 8:
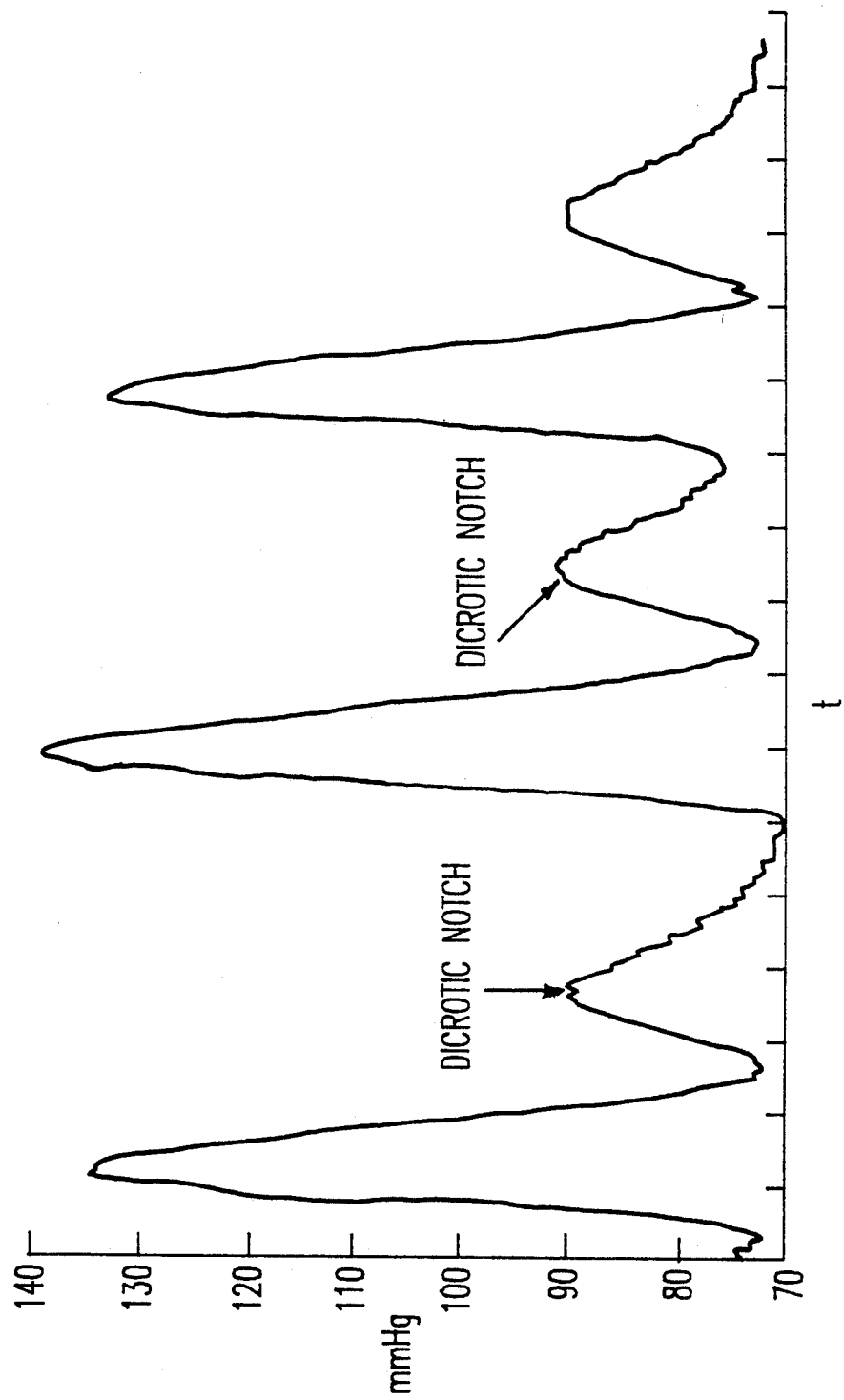
FIG. 8 illustrates various dicrotic notches following the systolic portions of the blood pressure signal.

FIG. 6 illustrates the signal overshoot time which is indicated by the period between the peak of the systolic portion of the signal to the time of appearance of the dicrotic notch. The signal rise time is defined as the period of time corresponding to the beginning of the systolic period to the peak pressure point. FIG. 7 illustrates first and second overshoot portions associated with the run-off period during the diastolic portion of the signal. FIG. 7 shows the overshoot (which is the actual systolic pressure of the signal), where the overshoot appears similar to an additional notch. When such appears, its location will be between the actual dicrotic notch (2) and the peak of the signal. FIG. 8 shows a series of dicrotic notch points following the pressure peaks for the situation where there is no overshoot observed. Three consecutive signals are illustrated in FIG. 8. In FIG. 8 the notch is shown and there is no overshoot.

Figure 9:
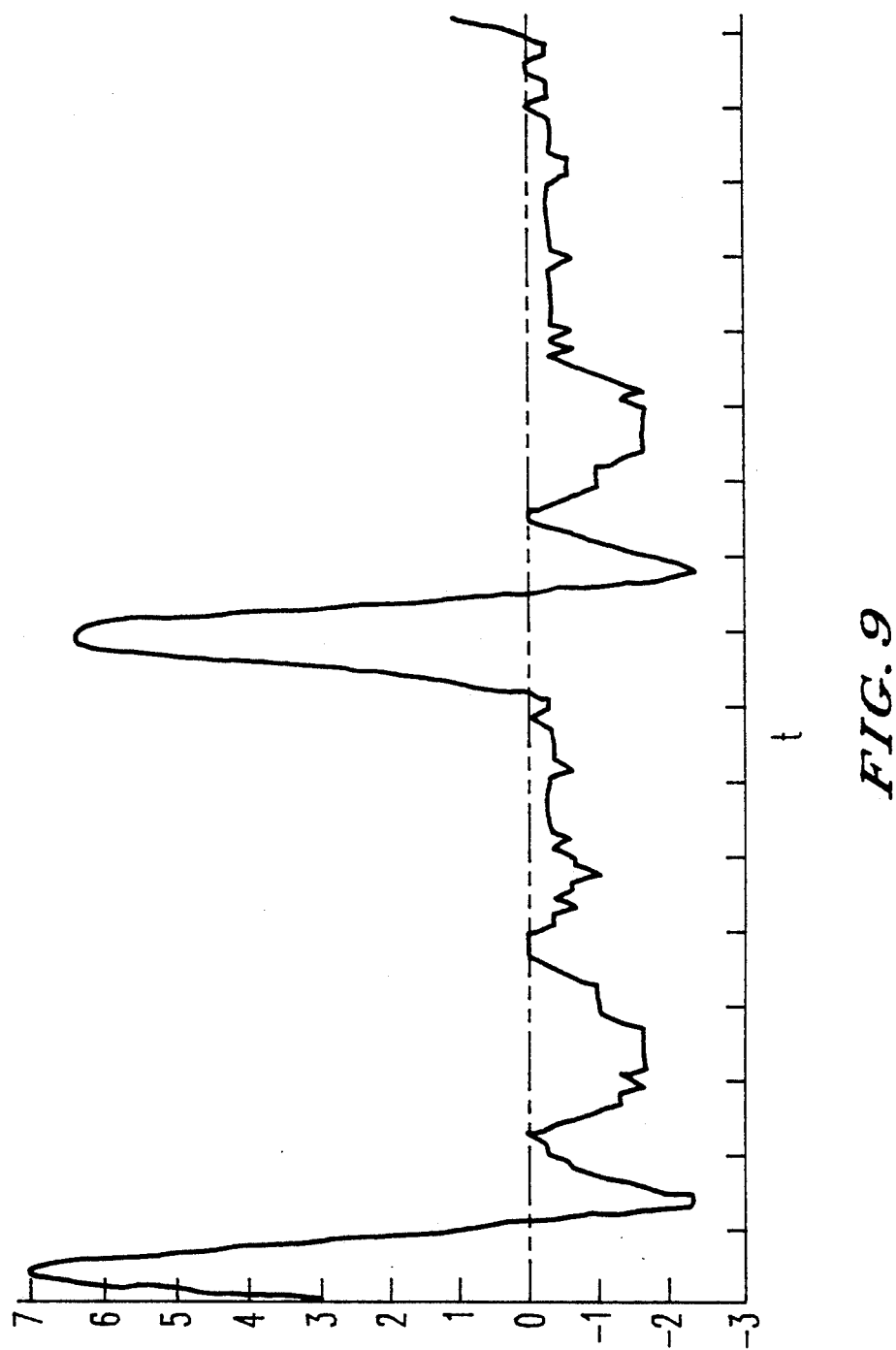
FIG. 9 shows a waveform representative of the first derivative of the analyzed blood pressure signal.
Figure 10:
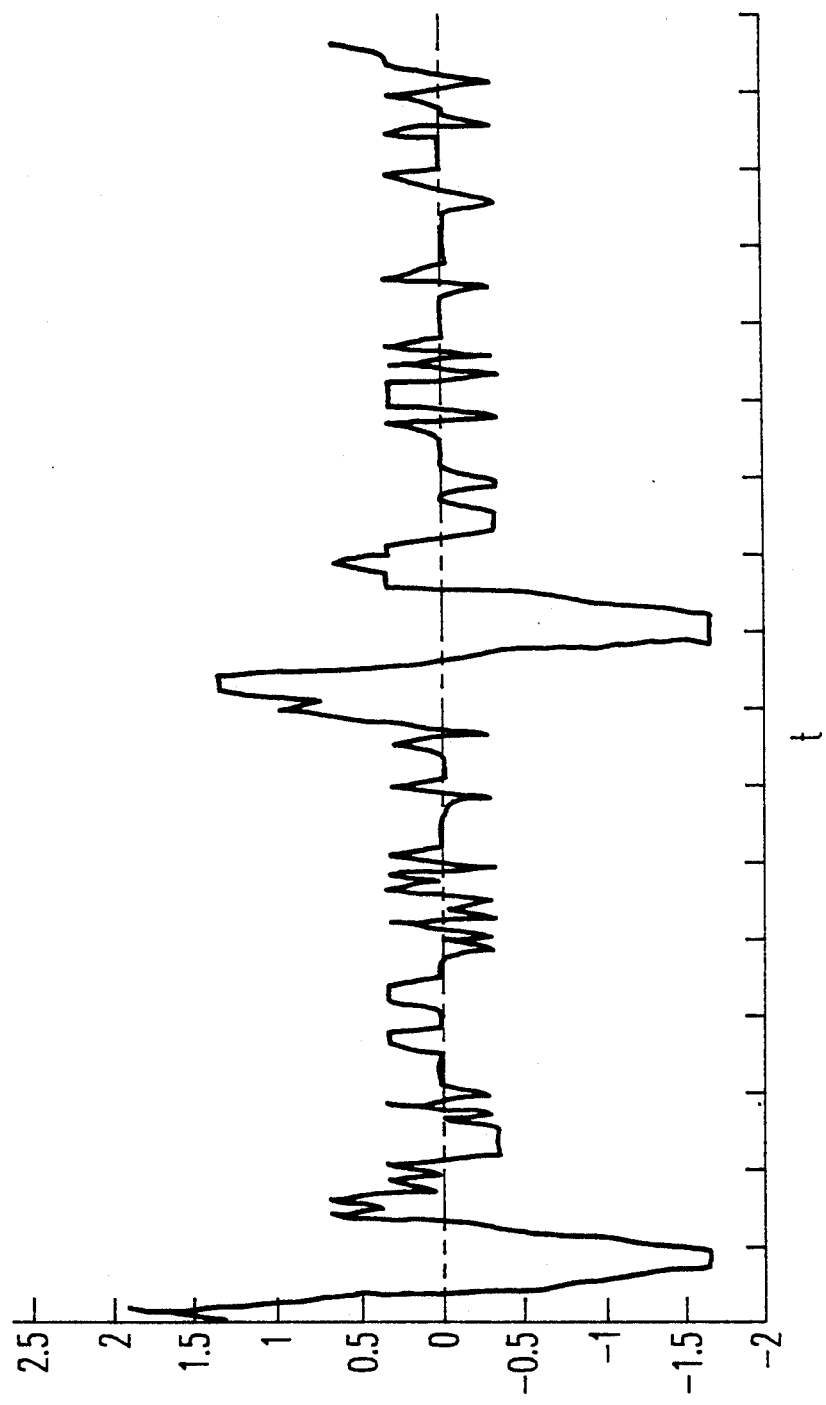
FIG. 10 illustrates the second derivative of the blood pressure signal, which is the first derivative of the signal shown in FIG. 9.

FIGS. 9 and 10 show the first and second differentiations of the arterial waveform, respectively. As can be seen from FIG. 9, the high points of the first derivative correspond to the initial portions of the systolic period where the rate of change of the increasing pressure is greatest. Similarly, at the low point of the diastolic portion of the signal (where the slope is close to zero) the first derivative will show a low point which is then followed by a peak at reference point zero and then a decrease in the differentiated value. FIG. 10 illustrates that in the second derivative there a number of peaks on either side of reference point zero following each pair of high and low points associated with the peak pressure and low point in pressure of the diastolic portions.

The cardiac output and SVR of the patient are obtained as follows:

$$Co = \frac{a[\sqrt{|s|} \cdot h^2 \cdot m^{\frac{3}{2}} \cdot f^{\frac{3}{2}} \cdot d^3 \cdot BSA \cdot \log(a)]}{\sqrt{f} \cdot i \cdot \log(i) \cdot (m-n)^{\frac{3}{2}} \cdot \sqrt{pr} \cdot \log(t)}$$

where $\alpha$ is a constant, s represents the minimum peak of the second derivative, h is the rise time of the signal, m is equal to the signal square root integral, n equals rise square root integral, f equals heart rate per minute, d is the amplitude of the waveform, BSA represents the patient's body surface area, a equals systolic peak pressure, i equals time interval between the point of maximum pressure of the systolic portion and the point at which the dicrotic notch is detected, p equals the maximum value of the first derivative, r equals the first maximum value of the second derivative, and t equals the second maximum value of the second derivative.

$$SVR = \frac{a[\sqrt{e} \cdot r^{\frac{3}{2}} \cdot b \cdot i^2 \cdot (m-n)^{\frac{5}{2}} \cdot p \cdot |q|]}{h^2 \cdot m^{\frac{5}{2}} \cdot d^2 \cdot \log(g) \cdot |s| \cdot \log|s| \cdot BSA}$$

where $\alpha$ is a constant, s represents the minimum peak of the second derivative, h is the rise time of the signal, m is equal to the signal square root integral, n equals rise square root integral, f equals heart rate per minute, d is the amplitude of the waveform, BSA represents the patient's body surface area, a equals systolic peak pressure, i equals time interval between the point of maximum pressure of the systolic portion and the point at which the dicrotic notch is detected, p equals the maximum value of the first derivative, r equals the first maximum value of the second derivative, and t equals the second maximum value of the second derivative.

In deriving the above calculations for cardiac output and SVR, the values are calculated for several systolic peaks (e.g. five or more) and the CO/SVR values are averaged. The cardiac output and SVR algorithm of the invention allow the use of a wide range of known non-invasive techniques for producing the waveforms of the patient's blood pressure, such as photoelectric and piezoelectric methods. The most accurate results are obtained from an invasive method, such as the use of catheters placed into various arteries, particularly a radial or femoral artery. Invasive pressure monitoring is now routinely performed at the patient's bedside which therefore allows continuous measurements of blood pressure and analysis of blood samples. Such a method is the most accurate because the data produces a minimum of artifacts. Furthermore, the use of blood pressure data such as systolic, diastolic and pulse pressure can be displayed on a beat-to-beat basis. Also, the use of piezoelectric or electrooptic sensors with the inventive method and apparatus is possible when invasive blood pressure procedures are undesirable. The advantage of these techniques is that they are completely non-invasive, but they are also less accurate.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by letters patent of the United States is:

1. A method for measuring cardiac output and system vascular resistance (SVR) of a patient by analyzing the patient's blood pressure signal waveform, wherein said waveform includes a plurality of successive peaks corresponding to a plurality of systolic and diastolic portions of the signal, comprising the steps of:
   (a) detecting an analog signal representative of the blood pressure of the patient;
   (b) converting said analog signal to a digital signal;
   (c) low-pass filtering said digital signal;
   (d) extracting a plurality of parameters from said filtered digital signal; and
   (e) calculating cardiac output and SVR values on the basis of said extracted parameters,
   wherein said step of extracting includes determining an interval of time between a point of maximum pressure of a systolic portion of said blood pressure signal waveform and a point at which a first dicrotic notch following said point of maximum pressure is detected.

2. The method for measuring cardiac output and SVR of a patient according to claim 1, further comprising the step of inputting a BSA value which represents the body surface area of the patient, for use in the step of calculating said cardiac output and said SVR values.

3. The method for measuring cardiac output and SVR of a patient according to claim 1, further comprising the step of displaying the cardiac output and SVR of the patient.

4. The method for measuring cardiac output and SVR of a patient according to claim 1, wherein said step of extracting includes determining a point of minimum pressure of a diastolic portion of said blood pressure signal waveform following said systolic portion, a mean pressure value of said systolic and diastolic portions, and an amplitude of said waveform.

5. The method for measuring cardiac output and SVR of a patient according to claim 4, wherein said step of extracting further includes determining a heart rate, a pulse pressure value, and a time interval between the beginning of the systolic portion of said waveform and the peak of said systolic portion.

6. The method for measuring cardiac output and SVR of a patient according to claim 5, wherein said step of extracting further includes determining a signal square root integral and a rise square root integral of said blood pressure signal waveform.

7. The method for measuring cardiac output and SVR of a patient according to claim 6, wherein said step of extracting further includes determining maximum and minimum values of first and second derivatives of said blood pressure signal waveform.

8. The method for measuring cardiac output and SVR of a patient according to claim 7, wherein a patient's cardiac output is determined by the equation $$Co = \frac{a[\sqrt{|s|} \cdot h^2 \cdot m^{\frac{3}{2}} \cdot f^{\frac{3}{2}} \cdot d^3 \cdot BSA \cdot \log(a)]}{\sqrt{f} \cdot i \cdot \log(i) \cdot (m-n)^{\frac{3}{2}} \cdot \sqrt{pr} \cdot \log(t)}$$

where $a$ is a constant, s represents the minimum peak of the second derivative, h is the rise time of the signal, m is equal to the signal square root integral, n equals rise square root integral, f equals heart rate per minute, d is the amplitude of the waveform, BSA represents the patient's body surface area, a equals systolic peak pressure, i equals time interval between the point of maximum pressure of the systolic portion and the point at which the dicrotic notch is detected, p equals the maximum value of the first derivative, r equals the first maximum value of the second derivative, and t equals the second maximum value of the second derivative.

9. The method for measuring cardiac output and SVR of a patient according to claim 7, wherein the patient's system vascular resistance is calculated by the equation $$SVR = \frac{a[\sqrt{e} \cdot r^{\frac{3}{2}} \cdot b \cdot i^2 \cdot (m-n)^{\frac{5}{2}} \cdot p \cdot |q|]}{h^2 \cdot m^{\frac{5}{2}} \cdot d^2 \cdot \log(g) \cdot |s| \cdot \log|s| \cdot BSA}$$

where $a$ is a constant, e equals the average amplitude of the systolic and diastolic portions, r equals the first maximum value of the second derivative, b equals the diastolic pressure, i equals the time interval between the point of maximum pressure of the systolic portion and the point at which the dicrotic notch is detected, m equals the signal square root integral, n equals the rise square root integral, p equals the maximum peak of the first derivative, q equals the minimum peak of the first derivative, h equals the rise time of the integral, d equals the amplitude of the signal waveform, g equals systolic minus diastolic pressure, s equals the minimum peak of the second derivative, and BSA equals the body surface area of the patient.

10. A system for measuring cardiac output and system vascular resistance (SVR) of a patient by analyzing a blood pressure signal waveform of the patient, comprising:

means for detecting an analog signal representative of the blood pressure of the patient;

means for converting said analog signal to a digital signal;

means for low-pass filtering said digital signal;

means for extracting a plurality of parameters from said filtered digital signal; and means for calculating a cardiac output value and an SVR value on the basis of said extracted parameters, wherein said means for extracting includes a means for determining an interval of time between a point of maximum pressure of a systolic pressure of said blood pressure signal waveform and a point at which a first dicrotic notch following said point of maximum pressure is detected.

11. The system for measuring cardiac output and SVR of a patient according to claim 10, further comprising means for inputting a BSA value which represents the body surface area of the patient for use by the calculating means for calculating said cardiac output and said SVR.

12. The system for measuring cardiac output and SVR of a patient according to claim 10, further comprising a means for displaying the cardiac output and SVR of the patient.

13. The system for measuring cardiac output and SVR of a patient according to claim 10, wherein said means for extracting includes a means for determining a point of minimum pressure of the diastolic portion of said blood pressure signal waveform following said systolic portion, a mean pressure value of said systolic and diastolic portions, and an amplitude of said waveform.

14. The system for measuring cardiac output and system vascular resistance of a patient according to claim 13, wherein said means for extracting further includes means for determining a heart rate, a pulse pressure, and a time interval between the beginning of the systolic portion of said waveform and the peak of said systolic portion.

15. The system for measuring cardiac output and SVR of a patient according to claim 14, wherein said means for extracting further includes a means for determining a signal square root integral and a rise square root integral of said blood pressure signal waveform.

16. The system for measuring cardiac output and SVR of a patient according to claim 15, wherein said means for extracting further includes a means for determining the maximum and minimum values of first and second derivatives of said blood pressure signal waveform.

17. The system for measuring cardiac output and SVR o a patient according to claim 16, wherein a patient's cardiac output is determined by the equation $$C_o = \frac{\alpha[\sqrt{|s|} \cdot h^2 \cdot m^{\frac{3}{2}} \cdot f^{\frac{3}{2}} \cdot d^3 \cdot BSA \cdot \log(a)]}{\sqrt{f} \cdot i \cdot \log(i) \cdot (m-n)^{\frac{3}{2}} \cdot \sqrt{pr} \cdot \log(t)}$$

where $\alpha$ is a constant, s equals the minimum peak of the second derivative, h equals the rise time of the signal, m equals signal square root integral, n equals rise square root integral, f equals heart rate per minute, d equals amplitude of the waveform, BSA equals the patient's body surface area, a equals systolic peak pressure, i equals time interval between the point of maximum pressure of the systolic portion and the point at which the dicrotic notch is detected, p equals the maximum value of the first derivative, r equals the first maximum value of the second derivative, and t equals the second maximum value of the second derivative.

18. The system for measuring cardiac output and SVR of a patient, according to claim 16, wherein the patient's SVR is calculated by the equation $$SVR = \frac{\alpha[\sqrt{e} \cdot r^{\frac{3}{2}} \cdot b \cdot i^2 \cdot (m-n)^{\frac{5}{2}} \cdot p \cdot |q|]}{h^2 \cdot m^{\frac{5}{2}} \cdot d^2 \cdot \log(g) \cdot |s| \cdot \log|s| \cdot BSA}$$

where $\alpha$ equals a constant, e equals the average amplitude of the systolic and diastolic portions, r equals the first maximum value of the second derivative, b equals the diastolic pressure, i equals the time interval between the point of maximum pressure of the systolic portion and the point at which the dicrotic notch is detected, m equals the signal square root integral, n equals the rise square root integral, p equals the maximum peak of the first derivative, q equals the minimum peak of the first derivative, h equals the rise time of the integral, d equals the amplitude of the signal waveform, g equals systolic minus diastolic pressure, s equals the minimum peak of the second derivative, and BSA equals the body surface area of the patient.

* * * * *